(12) United States Patent
Javitt

(10) Patent No.: US 10,881,665 B2
(45) Date of Patent: Jan. 5, 2021

(54) FORMULATIONS FOR TREATMENT OF POST-TRAUMATIC STRESS DISORDER

(71) Applicant: Glytech LLC, Ft. Lee, NJ (US)

(72) Inventor: Daniel C. Javitt, Ft. Lee, NJ (US)

(73) Assignee: GLYTECH, LLC, Ft. Lee, NJ (US)

( * ) Notice: Subject to any disclaimer, the term of this patent is extended or adjusted under 35 U.S.C. 154(b) by 0 days.

(21) Appl. No.: 15/987,933

(22) Filed: May 24, 2018

(65) Prior Publication Data

US 2018/0338983 A1 Nov. 29, 2018

Related U.S. Application Data

(60) Provisional application No. 62/518,020, filed on Jun. 12, 2017, provisional application No. 62/510,801, filed on May 25, 2017.

(51) Int. Cl.

| | | |
|---|---|---|
| *A61K 31/55* | (2006.01) | |
| *A61K 31/554* | (2006.01) | |
| *A61K 47/40* | (2006.01) | |
| *A61K 31/4525* | (2006.01) | |
| *A61P 25/00* | (2006.01) | |
| *A61K 9/00* | (2006.01) | |
| *A61K 31/135* | (2006.01) | |
| *A61K 31/4152* | (2006.01) | |
| *A61K 45/06* | (2006.01) | |
| *A61P 25/22* | (2006.01) | |
| *A61P 25/24* | (2006.01) | |
| *A61K 31/165* | (2006.01) | |
| *A61K 31/42* | (2006.01) | |
| *A61K 31/496* | (2006.01) | |

(52) U.S. Cl.
CPC ............ *A61K 31/55* (2013.01); *A61K 9/0019* (2013.01); *A61K 31/135* (2013.01); *A61K 31/165* (2013.01); *A61K 31/4152* (2013.01); *A61K 31/42* (2013.01); *A61K 31/4525* (2013.01); *A61K 31/496* (2013.01); *A61K 31/554* (2013.01); *A61K 45/06* (2013.01); *A61K 47/40* (2013.01); *A61P 25/00* (2018.01); *A61P 25/22* (2018.01); *A61P 25/24* (2018.01); *A61K 9/0053* (2013.01); *A61K 2300/00* (2013.01)

(58) Field of Classification Search
CPC .. A61K 31/4152; A61K 31/135; A61K 31/42; A61P 25/00; A61P 25/22; A61P 25/24
See application file for complete search history.

(56) References Cited

U.S. PATENT DOCUMENTS

| | | |
|---|---|---|
| 6,391,922 B1 | 5/2002 | Fogel |
| 6,689,816 B2 | 2/2004 | Fogel |
| 2005/0209218 A1 | 9/2005 | Meyerson et al. |
| 2010/0016403 A1 | 1/2010 | Higgins et al. |
| 2010/0216805 A1 | 8/2010 | Barlow et al. |
| 2014/0018349 A1 | 1/2014 | Heresco-Levy et al. |

FOREIGN PATENT DOCUMENTS

| | | |
|---|---|---|
| WO | 2013163562 A2 | 10/2013 |
| WO | 2014011590 A2 | 1/2014 |
| WO | 2016049048 A1 | 3/2016 |
| WO | 2017024129 A1 | 2/2017 |

OTHER PUBLICATIONS

Difede et al. Neuropsychopharmacology. 2014, vol. 39, pp. 1052-1058 (Year: 2014).*
Attari et al. J. Res. Med. Sci., 2014, vol. 19, No. 7, pp. 1-11 (Year: 2014).*
Heresco-Levy, Uriel, et al. "Pilot-controlled trial of D-cycloserine for the treatment of post-traumatic stress disorder." International Journal of Neuropsychopharmacology 5.4 (2002): 301-307.
Steckler, Thomas, and Victoria Risbrough. "Pharmacological treatment of PTSD—established and new approaches." Neuropharmacology 62.2 (2012): 617-627.
Rodrigues, Helga, et al. "Does D-cycloserine enhance exposure therapy for anxiety disorders in humans? A meta-analysis." PloS one 9.7 (2014): e93519.

* cited by examiner

*Primary Examiner* — James D. Anderson
(74) *Attorney, Agent, or Firm* — JMB Davis Ben-David

(57) ABSTRACT

Provided herein are compositions for reducing symptoms of post-traumatic stress disorder. The compositions include a combination of an N-methyl-D-aspartate (NMDA) receptor antagonist and an anti-depression agent.

10 Claims, 3 Drawing Sheets

FORMULATIONS FOR TREATMENT OF POST-TRAUMATIC STRESS DISORDER

CROSS-REFERENCE TO RELATED APPLICATIONS

Benefit is claimed to U.S. Provisional Patent Application No. 62/510,801, filed May 25, 2017, and U.S. Provisional Patent Application No. 62/518,020, filed Jun. 12, 2017; the contents of both of which are incorporated by reference herein in their entirety.

FIELD

Provided herein are compositions that include a combination of an N-methyl-D-aspartate (NMDA) receptor antagonist and an anti-depression agent for reducing symptoms of post-traumatic stress disorder (PTSD). Methods of PTSD treatment using the described compositions are also described.

BACKGROUND

Post-traumatic stress disorder (PTSD) is a severe neuropsychiatric disorder that affects 1-15% of individuals worldwide, including 10-60% of combat veterans. Diagnosis of PTSD may be determined using criteria described in standard textbooks of the art, such as the Diagnostic and Statistical Manual of Mental Disorders-fifth edition (DSM-5) published by the American Psychiatric Association.

PTSD is defined as the development of characteristic and persistent symptoms along with difficulty functioning after exposure to situations known to induce severe stress, including death, threatened death, actual or threatened serious injury or actual or threatened sexual violence. The stressful situation may be experienced either directly or indirectly Characteristic and persistent symptoms include re-experiencing symptoms, avoidance symptoms, and increased arousal. These are described in Alexander, "Pharmacotherapy for Post-traumatic Stress Disorder In Combat Veterans: Focus on Antidepressants and Atypical Antipsychotic Agents," *P T.* 37(1):32-8, 2012 PMC3278188, among others. Symptoms of PTSD can be rated using standardized scales such as versions of the Clinician administered PTSD scale (CAPS). These scales can be used to determine criteria for response and remission.

PTSD can be divided into acute vs. chronic subtypes. In general, symptoms lasting less than 3 months are considered to be acute, whereas symptoms lasting greater than 3 months are considered chronic.

Symptoms of PTSD may also be categorized as re-experiencing, active avoidance, emotional numbing, dysphoric arousal, and anxious arousal. Re-experiencing can refer to both positive and negative events. Both positive and negative dissociation may also occur.

Symptoms of PTSD may also be categorized into intrusion, avoidance and hyperarousal categories using scales such as the Impact of Event Scale-Revised. Other subdivisions of PTSD symptoms may also be proposed.

Differences in the severity of PTSD symptoms may be observed across individuals. These symptom types may respond differentially to specific types of pharmacological or behavioral intervention.

In addition to the symptoms described above, rates of suicide are increased among individuals suffering from PTSD. Similarly, rates of major depression are significantly elevated among individuals with PTSD.

Among individuals diagnosed with PTSD, lifetime risk of suicide attempt may be as high as 25%. Likelihood to commit suicide may be assessed using standard instruments such as the Columbia Suicide Severity Rating Scale. Separate ratings may be obtained for suicidal ideation and suicidal behavior.

Major depression is a clinical syndrome that includes a persistent sad mood or loss of interest in activities, which persists for at least two weeks in the absence of treatment. Symptoms of major depression are typically measured using rating scales such as the Hamilton Depression Rating Scale (HAM-D), the Montgomery Asburg Depression Rating Scale (MADRS) or the Beck Depression Inventory (BDI). In addition to including symptoms relevant to depressed mood, the HAM-D also contains symptoms sensitive to psychosis, including items for guilt, depersonalization/derealization and paranoia. Depression may be studied in animal models such as the forced swim test.

Symptoms of PTSD can be modeled using rodent assays of re-experiencing, avoidance and arousal symptoms. One effective model is the Wistar-Kyoto (WKY) conditioned fear model (e.g. Laitman et al., "The alpha1 adrenoceptor antagonist prazosin enhances sleep continuity in fear-conditioned Wistar-Kyoto rats," *Prog Neuropsychopharmacol Biol Psychiatry* 49:7-15. 2014, PMC3969852).

For treatment of PTSD, clinicians currently employ one or more agents also used in treatment of depression and/or psychosis. Such pharmaceutical agents include selective serotonin reuptake inhibitors (SSRI), serotonin/norepinephrine (SNRI) reuptake inhibitors, and atypical antipsychotics including sertraline, paroxetine, venlafaxine, and quetiapine. The tetracyclic antidepressant mirtazapine has been shown to be effective as an adjunctive agent to SSRIs and SNRIs.

Nevertheless, such agents are only partially effective and do not produce full symptom remission in most individuals. Similarly, the NMDAR antagonist ketamine is reported to produce improvements in some aspects of PTSD following single intravenous dosing. However, its utility is limited by psychotomimetic effects, and neurotoxicity during repeated administration. Effects of ketamine have not been tested in combination with SSRIs, SNRIs, atypical antipsychotics or other therapeutic medications. Thus, a continuing need exists for the development of treatments for PTSD.

SUMMARY

Described herein are formulations containing an NMDAR antagonist, combined, in certain embodiments, with an anti-depression or anti-psychosis agent, and methods for use of such agents in the treatment of PTSD and symptoms of PTSD.

In a particular embodiment, the NMDAR antagonists may be drawn from competitive antagonists of the NMDAR. In other embodiments, the NMDAR antagonists may be drawn from agents that serve as antagonists at the glycine, glutamate or redox/polyamine recognition sites. In still other embodiments, the NMDAR antagonists may be non-selective antagonists or selective antagonists at NMDAR containing specific subunits such as the NR2A or NR2B subunits.

In one embodiment, described herein is an oral dosage regimen consisting essentially of two therapeutic agents, wherein a first of said two active ingredients is an NMDAR antagonist and the second is an antidepressant or atypical antipsychotic agent.

In one embodiment, the first therapeutic agent consists of D-cycloserine, administered at a dosage of ≥500 mg/d to ≤1000 mg/d, and formulated to produce blood levels in excess of 25 microgram (μg)/mL. Such net-antagonist dosages of D-cycloserine include in certain embodiments, a dosage of equal or greater than 10 mg/kg.

In some embodiments, the antagonist of the glycine site of the NMDAR is drawn from a list that includes gavestinel, rapastinel (GlyX-13), apimostinel (NRX-1074), AV-101, Cerc-301 and D-cycloserine formulated to produce plasma concentrations greater than 25 μg/mL.

In some embodiments, the first therapeutic agent is a competitive antagonist of the NMDAR. In some embodiments, the first therapeutic agent is drawn from a list that includes gavestinel, D-CPPene, ketamine, dextromethorphan, CNS-1102, AZD6765, or CGS-19755.

In some embodiments, the second therapeutic agent comprises a tetracyclic antidepressant (TeCA), selective serotonin reuptake inhibitor (SSRI), a serotonin/norepinephrine reuptake inhibitor (SNRI) a Noradrenaline and specific serotonin agent (NaSSa), an atypical antidepressant, a 5-HT2A antagonist or a combination thereof.

In some embodiments, the second therapeutic agent is drawn from a list that includes sertraline, paroxetine or quetiapine.

In some embodiments, the antidepressant is drawn from a list that includes imipramine, amitryptyline, amoxapine, bupropion, citalopram, clomipramine, desipramine, desvenlafaxine, duloxetine, escitalopram, fluoxetine, fluvoxamine, levomilnacipran, maprotiline, mianserin, milnacipran, levomilnacipran, mirtazapine, nefazodone, paroxetine, sertraline, setiptiline, trazodone, venlafaxine, venlafaxine XR, dapoxetine, indalpine, vilazodone and vortioxetine.

In some embodiments, the anti-depression agent is drawn from a list that includes S-(+)-mirtazapine or R-(−)-mirtazapine.

In particular embodiments, the second agent is a selective 5-HT2A receptor antagonist or inverse agonist.

In some embodiments, the second agent is drawn from a list that includes volinanserin (MDL100,907, also known as M100907) pruvanserin (EMD281014), eplivanserin (SR-46349, Citryri), CYR-101 and pimavanserin (ACP-103).

In some embodiments, the second therapeutic agent is drawn from a list that includes aglomelatine, Lu AA21004, F2695, SEP-227162, LuAA24530, SEP-225289, Eplivanserine, SR46349, LY12624803, HY10275, TIK-301/LY156735, Lonasen, LU-31-130, SLV313, Edivoxetine, OPC-34712, lisdexamfetamine, sacomeline, clouracetam, BMS-82036 and M100907.

In some embodiments, the combination of an NMDAR antagonist and an anti-depressant medication is administered following initial treatment with parenteral ketamine administration, such as intravenous, intranasal or subcutaneous administration. In some embodiments, the specific enantiomers S-ketamine or R-ketamine are used for initial treatment.

Also described herein ate pharmaceutical compositions including a net antagonist effective amount of D-cycloserine; and R-(−)-mirtazapine, in which the net antagonist effective amount of D-cycloserine is a dosage ≥500 mg/d to ≤1000 mg/d, and formulated to produce blood levels in excess of 25 microgram (μg)/mL, and which in particular embodiments is D-cycloserine provided at a dosage of equal or greater than 10 mg/kg.

The foregoing and other objects, features, and advantages will become more apparent from the following detailed description.

DETAILED DESCRIPTION

I. Terms

Figure 1:
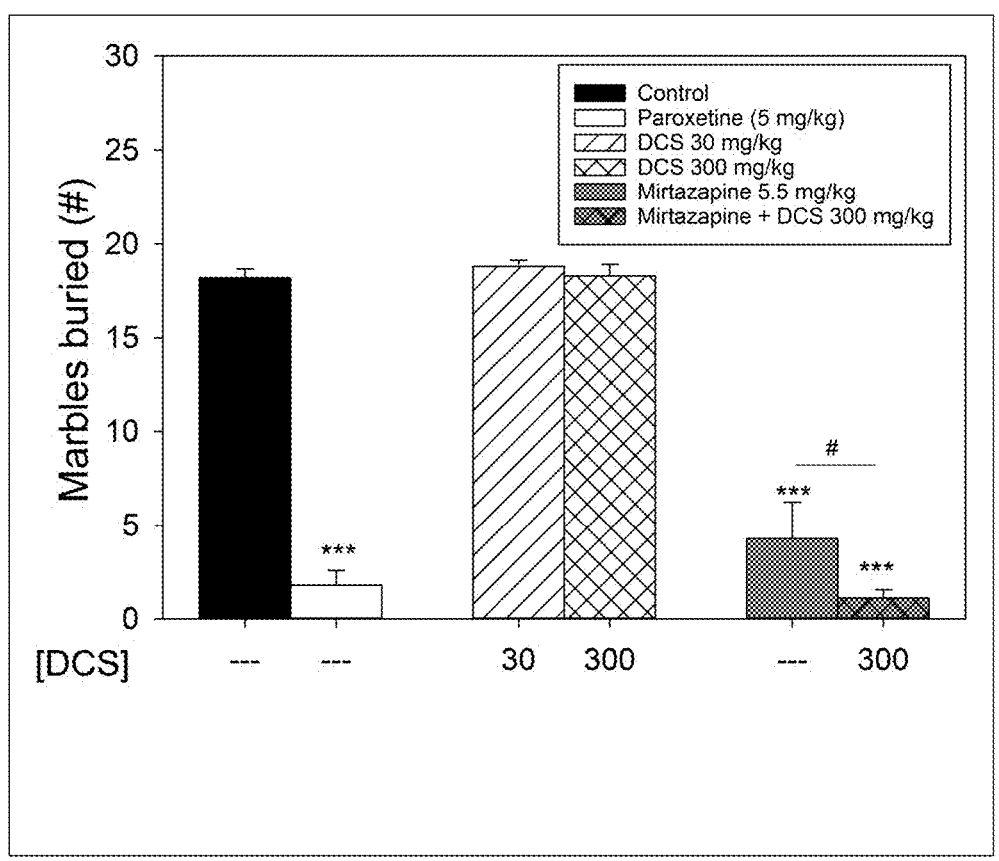
FIG. 1 shows the synergistic effects of DCS and mirtazapine on marble burying ***p<0.001 vs. Vehicle. #p<0.05 mirtazapine+DCS 300 mg/kg vs. mirtazapine alone. 10 mice were treated with either Vehicle (control), Paroxetine (5 mg/kg), Mirtazapine (5.5 mg/kg), D-cycloserine (30 mg/kg), D-cycloserine (300 mg/kg) or D-cycloserine (300 mg/kg)+(Mirtazapine 5.5 mg/kg) which was administered by IP 30 minutes prior to test. Distance traveled during the test was captured by cameras and quantified using Video Tracker Software (ViewPoint Life Sciences Software, France). At the end of the test mice were removed from the cages and the number of unburied marbles was counted. A marble was considered buried if it was covered at least two thirds with bedding. An effect was considered significant if p<0.05.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." "Consisting essentially of" indicates a composition, method, or process that includes only those listed features as the active or essential elements, but can include non-active elements in addition. The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

As used herein, reference to an "effective" amount or a "therapeutically effective amount" of therapeutic agents referenced herein, it is meant a nontoxic but sufficient amount of the same to provide the desired effect. In a combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual.

Symptoms of PTSD include re-experiencing, active avoidance, emotional numbing, dysphoric arousal, and anxious arousal. Re-experiencing can refer to both positive and negative events. Both positive and negative dissociation may also occur. Symptoms of PTSD can also be categorized into intrusion, avoidance and hyperarousal categories using scales such as the Impact of Event Scale-Revised. The compositions and methods described herein can be used to treat these and other symptoms associated with PTSD.

D-cycloserine, or DCS, refers to the chemical D-cycloserine (CA Index Name: 3-Isoxazolidinone, 4-amino-, (4R)-(9CI); CAS Registry No. 68-41-7), or pharmaceutically acceptable salts thereof. DCS is an FDA (United States Food and Drug Administration)-approved drug for treatment of tuberculosis, and is sold by Eli Lilly and Company under the trade name Seromycin®. DCS is a structural analog of D-alanine, and is a broad-spectrum antibiotic produced by some strains of *Streptomyces orchidaceus* and *S. garphalus*.

II. Methods for Treatment of PTSD

Described herein are oral or parenteral dosage regimens for use in methods of treatment of PTSD, and symptoms thereof such as re-experiencing, avoidance, and/or increased arousal.

One embodiment of the described methods includes administering to a subject in need thereof a therapeutically effective amount of an N-methyl-D-aspartate receptor (NMDAR) antagonist.

In another embodiment, provided herein is an oral dosage regimen for use in methods for treating PTSD, or symptoms thereof, wherein the dosage regimen includes two therapeutic agents (active ingredients). The first of the active ingredients is an NMDAR antagonist and the second is an antidepressant or atypical antipsychotic agent.

NMDARs are a type of neuronal receptor for the brain neurotransmitter glutamate. NMDARs participate in a range of brain functions including sensory processing, cognition, and emotion regulation. NMDARs are comprised of multiple subunits termed GluN1, GluN2 and GluN3 (formerly NR1, NR2, NR3). Multiple forms of GluN1, GluN2 and GluN3 exist. An NMDAR may consist of various combinations of GluN1, GluN2 and GluN3 subunits in various amounts. Agonists and antagonists may affect all NMDARs equivalently, or may be selective for an NMDAR containing specific subunit types. The methods described herein include use of NMDAR antagonists.

NMDARs contain binding sites for the neurotransmitter glutamate and for the endogenous modulatory amino acids glycine and D-serine. NMDARs also are sensitive to the redox state of the surrounding tissue via a redox site/polyamine binding site.

Agents that bind to these sites and reduce NMDAR activity are termed competitive inhibitors.

The NMDAR glutamate binding site selectively binds the synthetic glutamate derivative N-methyl-D-aspartate with high affinity. This site is alternately referred to as the glutamate recognition site or the NMDA recognition site of the NMDAR.

The NMDAR glycine/D-serine binding site has been referred to as the glycine modulatory site, the allosteric modulatory site or the glycine-B receptor.

NMDARs form an ion channel that is blocked by several drugs of abuse, such as phencyclidine (PCP), ketamine, or dizocilpine (MK-801). These compounds bind to a site that has been termed the PCP receptor. Agents that block the NMDAR-associated ion channel are collectively termed non-competitive NMDAR antagonists, or NMDAR channel blockers. Blockade of NMDARs by channel blockers leads to a clinical psychotic state that closely resembles schizophrenia.

In the described methods, NMDARs may also be inhibited by antagonists that bind to the glutamate recognition sites, the glycine recognition site, or the polyamine binding site. Historically, high affinity NMDAR antagonists have been used in multiple clinical settings.

Selfotel (CGS19755) is an example of an antagonist that binds to the glutamate recognition site. Several such compounds were developed for CNS indications such as stroke or epilepsy. When used at doses sufficient to significantly inhibit NMDAR, these compounds, like channel blockers, lead to clinical psychotomimetic symptoms.

Additional compounds that function as antagonists of the glutamate recognition site include aptiganel (Cerestat, CNS-1102) and related compounds as described in Reddy et al., J Med Chem 37:260-7. 1994). Additional compounds that function as antagonists of the glutamate recognition site include alpha.-amino-carboxylic acid and phosphonic acid functionalities separated by a variety of spacer units. An unembellished example is 2-amino-5-phosphonovaleric acid (AP5) (Watkins, J. C.; Evans, R. H., Annu. Rev. Pharmacol. Toxicol. 1981, 21, 165), which contains a saturated carbon chain. More complex examples, which contain elements enhancing structural rigidity and therefore potency, include CPP, cis-4-(phosphonomethyl)-2-piperidinecarboxylic acid (CGS-19755) (Lehman, J. et al., J. Pharmacol. Exp. Ther. 1988, 246, 65), and (E)-2-amino-4-methyl-5-phosphono-3-pentenoic acid (CGP-37849) (Schmutz, M. et al., Abs. Soc. Neurosci. 1988, 14, 864). See U.S. Pat. No. 7,345,032, issued Mar. 18, 2008 and U.S. Pat. No. 5,168,103, incorporated herein by reference in its entirety.

In the described methods, NMDARs may also be inhibited by antagonists that bind to the glycine recognition site. In a particular embodiment, such inhibition is by D-cycloserine, administered at an antagonist producing dosage.

D-cycloserine is an anti-tuberculosis medication that also acts as a partial glycine-site antagonist (aka mixed agonist/antagonist). D-cycloserine produces primarily agonist effects at doses up to approximately 100 mg, and primarily antagonist effects at doses above 500 mg, with intermediate effects at intermediate doses. Plasma concentrations associated with primarily agonist effects are primarily <10 µg/mL. Plasma concentrations associated with antagonist effects are >25 µg/ml. Increased liability for toxicity is observed at plasma levels >35 µg/mL.

D-cycloserine is typically administered for the treatment of tuberculosis at doses of 250-1000 mg. Thus, typical doses are 250 mg, 500 mg, 750 mg or 1000 mg. Intermediate doses, such as 550, 600, 650, 700, 800, 850 or 900 mg are also possible. In particular embodiments of the described methods, D-cycloserine is administered to a subject at a dose of greater than 500 mg/day to less than or equal to 1000 mg/day, including but not limited to the above intermediate doses. Effective doses of D-cycloserine for the intended use in humans require sustained plasma levels exceed >25 ug/ml, which in particular embodiments is provided by a dosage of equal or greater than 10 mg/kg in an adult subject, such as 10-25 mg/kg/day. The described compositions can include D-cycloserine provided at a weight-based dose of between 10-25 mg/kg/day, such as but not limited to 12, 14, 15, 16, 20, 22, and 24 mg/kg/day. Achievement of these levels requires human doses in excess of 500 mg/day, which in an average adult will be about 700 mg/day. Human dosing of D-cycloserine to produce net antagonist effects can be understood from human pharmacokinetics studies.

Pharmacokinetics (PK) of D-cycloserine in humans after a dose of 500 mg have been previously studied. Critical parameters include maximum (peak) concentration achieved (Cmax), time to maximum concentration (Tmax) and area under the curve (AUC) during the dosing interval.

For example, Zhu et al. (Zhu M, Nix D E, Adam R D, Childs J M, Peloquin C A. Pharmacokinetics of cycloserine under fasting conditions and with high-fat meal, orange juice, and antacids. Pharmacotherapy. 2001; 21(8):891-7) showed median Cmax values of 14.8 microgram/mL under fasting conditions, with a range of 12.1-30.6 microgram/mL. Median AUC levels over 24 hr were 214 microgram-hr/mL with a range of 163-352, corresponding to median sustained plasma levels of 8.9 microgram/mL with a range of 6.8-14.7 microgram/mL.

Park et al., (Park S I, Oh J, Jang K, Yoon J, Moon S J, Park J S, Lee J H, Song J, Jang I J, Yu K S, Chung J Y. Pharmacokinetics of Second-Line Antituberculosis Drugs after Multiple Administrations in Healthy Volunteers. Antimicrob Agents Chemother. 2015; 59(8):4429-35.) evaluated pharmacokinetics of 250 mg PO D-cycloserine given every 12 hrs, and observed mean Cmax values of 24.9 microgram/mL and a mean AUC over 12 hrs of 242.3 mg-h/L, corresponding to a mean plasma level of 20. 2 microgram/mL.

Hung et al., 2014 (Hung W Y, Yu M C, Chiang Y C, Chang J H, Chiang C Y, Chang C C, Chuang H C, Bai K J. Serum concentrations of cycloserine and outcome of multidrug-resistant tuberculosis in Northern Taiwan. Int J Tuberc Lung Dis. 2014; 18(5):601-6) evaluated PK levels during clinical treatment with DCS. Mean dose across subjects was 8.8 mg/kg, with the majority of subjects (n=27) receiving 500 mg/day DCS, and a minority either 750 mg/d (n=4) or 250 mg/d (n=2). DCS concentrations at 2 and 6 hr after dosing were 19.7 and 18.1 microgram/mL.

Thus, a consistent finding of human PK studies is that sustained plasma doses following 500 mg administration of D-cycloserine are consistently below 25 microgram/mL. As described herein, the anti-PTSD effects of D-cycloserine are observed at dosages above 25 microgram/mL. Accordingly, the daily dose for producing such plasma levels will necessarily be above 500 mg/day, as described above.

Felbamate is another example of a compound that may act via the glycine binding site, and which can be used in the described methods. When administered to humans, felbamate produces psychotic effects that limit its clinical utility (e.g. Besag F M, Expert Opin Drug Saf 3:1-8, 2004).

Gavestinel (GV-150,526) is another example of an antagonist at the glycine binding site for use as described herein. Other similarly useful compounds are described in DiFabrio et al., J Med Chem 40:841-50, 1997, which is hereby incorporated by reference. Other examples of glycine site antagonists that are suitable for use in the pharmaceutical compositions and methods described herein are those referred to in the following: U.S. Pat. No. 6,667,317 which was issued on Dec. 23, 2003; U.S. Pat. No. 6,080,743 which was issued Jun. 27, 2000; U.S. Pat. No. 5,990,108, which was issued on Nov. 23, 1999; U.S. Pat. No. 5,942,540, which issued on Aug. 24, 1999; World Patent Application WO 99/34790 which issued on Jul. 15, 1999; WO 98/47878, which was published on Oct. 29, 1998; World Patent Application WO 98/42673, which was published on Oct. 1, 1998; European Patent Application EP 966475A1, which was published on Dec. 29, 1991; World Patent Application 98/39327, which was published on Sep. 11, 1998; World Patent Application WO 98/04556, which was published on Feb. 5, 1998; World Patent Application WO 97/37652, which was published on Oct. 16, 1997; U.S. Pat. No. 5,837,705, which was issued on Oct. 9, 1996; World Patent Application WO 97/20553, which was published on Jun. 12, 1997; U.S. Pat. No. 5,886,018, which was issued on Mar. 23, 1999; U.S. Pat. No. 5,801,183, which was issued on Sep. 1, 1998; World Patent Application WO 95/07887, which was issued on Mar. 23, 1995; U.S. Pat. No. 5,686,461, which was issued on Nov. 11, 1997; U.S. Pat. No. 5,622,952, issued Apr. 22, 1997; U.S. Pat. No. 5,614,509, which was issued on Mar. 25, 1997; U.S. Pat. No. 5,510,367, which was issued on Apr. 23, 1996; European Patent Application 517,347A1, which was published on Dec. 9, 1992; U.S. Pat. No. 5,260, 324, which published on Nov. 9, 1993. The foregoing patents and patent applications are incorporated herein by reference in their entireties.

Other examples of glycine site antagonists that can be used in the pharmaceutical composition and methods described herein are N-(6,7-dichloro-2,3-dioxo-1,2,3,4-tetrahydro-quinoxalin-5-yl)-N-(2-hydroxy-ethyl)-methanesulfonamide and 6,7-dichloro-5-[3-methoxymethyl-5-(1-oxypyridin-3-yl)-[1,2,4]triazol-4-yl]-1,4-dihydro-quinoxaline-2,3-dione.

Additional NMDAR antagonists for use herein are described in Schiene et al., U.S. Pat. Appl. No. US2001/0306674 A1, which is incorporated herein by reference in its entirety, and include without being limited thereto, N-containing phosphonic acids, such as norvaline (AP5), D-norvaline (D-AP5), 4-(3-phosphono-propyl)-piperazine-2-carboxylic acid (CPP), D-(E)-4-(3-phosphonoprop-2-enyl) piperazine-2-carboxylic acid (D-CPPene), cis-4-(phosphonomethyl)-2-piperidine carboxylic acid (Selfotel, CGS 19755), SDZ-220581, PD-134705, LY-274614 and WAY-126090; quinolinic acids, such as kynurenic acid, 7-chloro-kynurenic acid, 7-chloro-thiokynurenic acid and 5,7-dichloro-kynurenic acid, prodrugs thereof, such as 4-chlorokynurenine and 3-hydroxy-kynurenine; 4-aminotetrahydrochinolin-carboxylates, such as L-689,560; 4-hydroxyquinolin-2(1H)-ones, such as L-701,324; quinoxalinediones, such as licostinel (ACEA-1021) and CGP-68, 730A; 4,6-dichloro-indole-2-carboxylate derivatives such as MDL-105,519, gavestinel (GV-150,526) and GV-196,771A; tricyclic compounds, such as ZD-9,379 and MRZ-2/576, (+)-HA-966, morphinan derivatives such as dextromethorphan and dextrophan; benzomorphans, such as BIII-277CL;

other opioids, such as dextropropoxyphene, ketobemidone, dextromethadone and D-morphine; amino-adamantanes, such as amantadine and memantine; amino-alkyl-cyclohexanes, such as MRZ-2/579; ifenprodil and ifenprodile-like compounds such as eliprodil and PD-196,860; iminopyrimidines; or other NMDA-antagonists such as nitroprusside, D-cycloserine, 1-aminocyclopropane-carboxylic acid, dizocilpine (MK 801) and its analogs, phencyclidine (PCP), ketamine ((R,S)-2-(2-Chlorphenyl)-2-(methylamino)cyclohexan-1-on), (R)-ketamine, (S)-ketamine, remacemide and its des-glycinyl-metabolite FPL-12,495, AR-R-15,896, methadone, sulfazocine, AN19/AVex-144, AN2/AVex-73, Besonprodil, CGX-1007, EAB-318, Felbamate and NPS-1407. NMDA-Antagonists are, for example, disclosed in "Analgesics," edited by H. Buschmann, T Christoph, E. Friderichs, C. Maul, B. Sundermann, 2002, Wiley-VCH Verlag GmbH & Co. KGaA, Weinheim, Germany, in particular pages 389-428. The respective parts of the description are hereby incorporated by reference and form part of the present disclosure.

Along with identified NMDAR antagonists, additional effective compounds can be identified using well-validated electrophysiological assays such as modulation of NMDA-receptor mediated responses to NMDA glutamate-site agonists, or radioreceptor assays, such as modulation of binding to the NMDA PCP-receptor channel binding site. Glycine site agonists and antagonists can also be distinguished based upon both electrophysiology and receptor binding from compounds such as phencyclidine (PCP) or ketamine that bind to the channel site. Partial agonists are defined as compounds that have reduced efficacy for inducing conformational change in receptors (typically 40-80%) relative to full agonists. Mixed agonists/antagonists are compounds that may induce agonist effects at low dose but antagonist effects at high dose.

The NMDAR antagonist ketamine is currently approved as an anesthetic agent. The putative low affinity NMDAR antagonist memantine is approved for use in dementia. Otherwise, NMDAR antagonists have no established clinical utility. In general, NMDAR antagonists are considered contraindicated for use in psychotic, anxiety or depressive disorders. For example, the NMDAR antagonist D-cycloserine is contraindicated by FDA for use in depression, severe anxiety or psychosis.

D-cycloserine has previously been studied for treatment of PTSD, but primarily at low doses (e.g. 50 mg) at which it is considered to act as an NMDAR agonist, and is used primarily as an adjunct to behavioral intervention. Its use as an NMDAR antagonist for treatment of PTSD has not been described prior to the current disclosure.

As indicated above, particular embodiments of the described treatments for treating PTSD, or symptoms thereof, include a dosage regimen that includes one or two primary therapeutic agents (active ingredients). The first of the active ingredients is an NMDAR antagonist and the second is an antidepressant or atypical antipsychotic agent.

In some embodiments of the described methods, the first therapeutic (NMDAR antagonist) agent acts at the glycine, glutamate or polyamine recognition sites.

In some embodiments, the first therapeutic agent acts at NMDAR containing NR2A subunits or NR2B subunits.

In some embodiments, the first therapeutic agent is D-cycloserine administered at a dosage greater than 500 mg/day, such as between 500 and 1000 mg/day, and is formulated to produce plasma levels in excess of 25 microgram/mL.

In some embodiments, the first therapeutic agent is drawn from a list that includes ketamine, Selfotel, aptiganel, CPP, CGP-37849, felbamate, Gavestinel N-(6,7-dichloro-2,3-dioxo-1,2,3,4-tetrahydro-quinoxalin-5-yl)-N-(2-hydroxyethyl)-methanesulfonamide and 6,7-dichloro-5-[3-methoxymethyl-5-(1-oxypyridin-3-yl)-[1,2,4]triazol-4-yl]-1,4-dihydro-quinoxa-line-2,3-dione, 4-(3-phosphonopropyl)-piperazine-2-carboxylic acid (CPP), D-(E)-4-(3-phosphonoprop-2-enyl)piperazine-2-carboxylic acid (D-CPPene), SDZ-220581, PD-134705, LY-274614 and WAY-126090; quinolinic acids, such as kynurenic acid, 7-chloro-kynurenic acid, 7-chloro-thiokynurenic acid and 5,7-dichloro-kynurenic acid, prodrugs thereof, such as 4-chlorokynurenine and 3-hydroxy-kynurenine; 4-aminotetrahydrochinolin-carboxylates, such as L-689,560; 4-hydroxyquinolin-2(1H)-ones, such as L-701,324; quinoxalinediones, such as licostinel (ACEA-1021) and CGP-68, 730A; 4,6-dichloro-indole-2-carboxylate derivatives such as MDL-105,519, gavestinel (GV-150,526) and GV-196,771A; tricyclic compounds, such as ZD-9,379 and MRZ-2/576, (+)-HA-966, morphinan derivatives such as dextromethorphan and dextrophan; benzomorphans, such as BIII-277CL; other opioids, such as dextropropoxyphene, ketobemidone, dextromethadone and D-morphine; amino-adamantanes, such as amantadine and memantine; amino-alkyl-cyclohexanes, such as MRZ-2/579; ifenprodil and ifenprodile-like compounds such as eliprodil and PD-196,860; iminopyrimidines; or other NMDA-antagonists such as nitroprusside, D-cycloserine, 1-aminocyclopropane-carboxylic acid, dizocilpine (MK 801) and its analogs, (R)-ketamine, (S)-ketamine, remacemide and its des-glycinyl-metabolite FPL-12, 495, AR-R-15,896, methadone, sulfazocine, AN19/AVex-144, AN2/AVex-73, Besonprodil, CGX-1007, EAB-318, and NPS-1407.

In some embodiments, the NMDAR antagonist is combined with an anti-depression agent or an atypical antipsychotic, also referred to herein as the "second therapeutic agent". Many such agents operate by modulation of serotonin (5-HT), norepinephrine and dopamine are neurotransmitter signaling.

Serotonin (5-HT), norepinephrine, and dopamine are neurotransmitters in brain thought to be involved in the etiology of neuropsychiatric disorders.

5-HT2A receptors are a type of receptor for the neurotransmitter serotonin (5-HT). 5-HT2A antagonists, such as those for use in the described methods, are compounds that inhibit effects of agonists such as serotonin on 5-HT2A receptors. Inverse agonists are compounds that, in addition, reduce activity below basal levels. 5-HT2A receptor antagonists can be non-selective for 5-HT2A vs. other serotonin receptors (e.g. 5-HT2C), or selective for 5-HT2A receptors. Selective 5-HT2A antagonists can be developed and characterized using standard assay procedures, such as those described in U.S. Pat. No. 7,713,995 issued on May 11, 2010, which is herein incorporated by reference in its entirety.

Agents that act as non-selective serotonin receptor antagonists include ritanserin, ketanserin, seganserin, and ICI-169369. Agents that act as selective 5-HT2A antagonists or inverse agonists include volinanserin (MDL100,907, also known as M100907) pruvanserin (EMD281014), eplivanserin (SR-46349, Citryri), CYR-101 and pimavanserin (ACP-103). Selective 5-HT2A receptor antagonists and inverse agonists are presently under development for treatment of both depression and psychosis and are viewed as potential antidepressant/antipsychotic agents, generally and for the purposed of the currently-disclosed methods.

Additional 5-HT2A receptor antagonists or inverse agonists are described in U.S. Pat. No. 7,875,632 which was issued on Jan. 25, 2011; U.S. Pat. No. 7,868,176 issued on Jan. 11, 2011; U.S. Pat. No. 7,863,296 issued on Jan. 4, 2011; U.S. Pat. No. 7,820,695 issued Oct. 26, 2010; and/or U.S. Pat. No. 7,713,995 issued May 11, 2010 which are herein incorporated by reference in its entirety.

The most commonly used pharmacological treatments for depression consist of selective serotonin reuptake inhibitors (SSRI) such as sertraline, fluxetine, citalopram, escitalopram, paroxetine, and fluvoxamine and serotonin/norepinephrine (SNRI) reuptake inhibitors such as duloxetine, venlafaxine, desvenlafaxine, milnacipran, and levomilnacipran. These agents work by modulating brain levels of monoamines, in particular norepinephrine and serotonin, and/or by blocking 5-HT2A receptors. Additional classes of agent that can be combined with an NMDAR receptor antagonist for the use in the methods described herein include Noradrenergic and Specific Serotonergic (NaSSAs) such as aptazapine, esmirtazapine, mianserin, mirtazapine and setiptiline/tecipitiine, and atypical antidepressants such as bupropion, nefazodone, vilazodone and vortioxetine.

Other agents approved for treatment of depression and which can be used in the disclosed treatments include atypical antipsychotics such as risperidone, olanzapine, quetiapine, quetiapine XR, aripiprazole, brexpiprazole and lurasidone. Other potential atypical antipsychotics include amisulpride, aripiprazole, asenapine, bioanserin, bifeprunox, cariprazine, clotiapine, clozapine, iloperidone, lumatoperone (ITI-007), lurasidone, mosaproamine, olanzapine, paliperidone, perospirone, quetiapine, remoxipride, risperidone, sertindole, sulpiride, ziprasidone, zotepine.

Certain examples of atypical antipsychotics may function as antagonists of both dopamine D2 and serotonin 5-HT2A receptors. Agents that act at both D2 and 5-HT2A receptors have been termed serotonin-dopamine antagonists (SDAs).

In particular embodiments of the described methods, the second therapeutic agent (for use in combination with the NMDAR antagonist) is any agent as herein described, for example, a tetracyclic antidepressant (TeCA), selective serotonin reuptake inhibitor (SSRI), a serotonin/norepinephrine reuptake inhibitor (SNRI), a Noradrenergic and Specific Serotonergic (NaSSAs), an atypical antidepressant, a 5-HT2A receptor antagonist, an atypical antipsychotic approved for use in treatment of depression or a combination thereof.

In some embodiments, the two active ingredients are provided in a single pharmaceutical composition, and in some embodiments, a kit or combined dispenser packet is contemplated containing each of the two active ingredients. It is to be understood that the current disclosure contemplates the co-administration of either of the two active ingredients to a subject, whether such administration is combined in a single formulation or in separate formulations and whether such administration is coincident or staggered.

In some embodiments, the methods for treating PTSD in a subject in need thereof, include use of an oral dosage regimen, as described.

In some embodiments of the described methods, the subject also suffers from depression or anxiety. In some embodiments, the invention provides a method for reducing the severity of depression and anxiety, along with symptoms of PTSD. However it should be emphasized that a patient suffering from PTSD, and who could benefit from the described methods, will not necessary also be suffering from depression or anxiety.

In some embodiments of the described methods, the subject also suffers from suicidality, including suicidal ideation or behavior. In some embodiments, the invention provides a method for reducing the severity of suicidality, along with symptoms of PTSD. However, it should be emphasized that a patient suffering from PTSD, and who could benefit from the described methods, will not necessary also be suffering from suicidality.

As described above, in particular embodiments, the NMDAR receptor antagonist agent is used in a single-agent formulation for treatment of PTSD, or symptoms thereof. In such embodiments, the NMDAR antagonist agent is administered at a dosage, which is considered to be suboptimal for treating depression in said subject when treating said subject.

The pharmaceutical compositions for use in the described methods can be administered to the subject by any, or a combination, of several routes, such as oral, intravenous, trans-mucosal (e.g., nasal, vaginal, etc.), pulmonary, transdermal, ocular, buccal, sublingual, intraperitoneal, intrathecal, intramuscular, or long term depot preparation. Solid compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, lipids, alginic acid, or ingredients for controlled slow release. Disintegrators that can be used include, without limitation, micro-crystalline cellulose, corn starch, sodium starch glycolate and alginic acid. Tablet binders that may be used include, without limitation, acacia, methylcellulose, sodium carboxymethylcellulose, polyvinylpyrrolidone (Povidone), hydroxypropyl methylcellulose, sucrose, starch, and ethylcellulose.

The compositions can be formulated to reduce gastric degradation of D-cycloserine or other constituents, for example by application of an enteric coating agent that reduces pH-dependent gastric hydrolysis. The compositions can also be formulated for extended release using standard approaches.

Liquid compositions for oral administration prepared in water or other aqueous vehicles can include solutions, emulsions, syrups, and elixirs containing, together with the active compound(s), wetting agents, sweeteners, coloring agents, and flavoring agents. Various liquid and powder compositions can be prepared by conventional methods for inhalation into the lungs of the patient to be treated.

Injectable compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, the compounds may be administered by the drip method, whereby a pharmaceutical composition containing the active compound(s) and a physiologically acceptable excipient is infused. Physiologically acceptable excipients may include, for example, 5% dextrose, 0.9% saline, Ringer's solution or other suitable excipients. For intramuscular preparations, a sterile composition of a suitable soluble salt form of the compound can be dissolved and administered in a pharmaceutical excipient such as Water-for-Injection, 0.9% saline, or 5% glucose solution, or depot forms of the compounds (e.g., decanoate, palmitate, undecylenic, enanthate) can be dissolved in sesame oil. Alternatively, the pharmaceutical composition can be formulated as a chewing gum, lollipop, or the like.

A subject undergoing treatment with the described methods can experience significant improvements in symptoms of PTSD. Relative to subjects treated with alternative treatments for PTSD, subjects treated according to the described methods will experience, in some embodiments, greater improvement, or more long-lasting improvement, as measured by any clinically recognized assessment method for PTSD (e.g., the CAPS Scale).

The following examples are provided to illustrate certain particular features and/or embodiments. These examples should not be construed to limit the disclosure to the particular features or embodiments described.

EXAMPLES

Example 1: Treatment of PTSD with NMDAR Antagonists and Anti-Depressants

This example shows that unexpectedly, NMDAR antagonists reduce re-experiencing, avoidance and increased arousal symptoms associated with PTSD. In particular, D-cycloserine given at a dose designed to produce NMDAR antagonist effects unexpectedly reduces re-experiencing, avoidance and increased arousal symptoms associated with PTSD. Similar effects are not observed with competitive NMDAR antagonists targeting the glutamate binding sites.

Inbred Wistar-Kyoto (WKY) rats have been used as models of several behavioral deficits, such as stress vulnerability and sleep disturbance. WKY rats also showed perseveration of avoidance after applying mild electric shock. In our validation studies with fear conditioning, WKY rats exhibited an obvious deficit in fear extinction compared to the Wistar rats. These evidences suggest WKY rats may be an ideal model in screening compounds which possesses potentials in treating psychiatric conditions of PTSD.

Fear memories are crucial in psychiatric conditions such as PTSD. Pavlovian fear conditioning (FC) test is a widely-used behavioral assay in rodents for measurement of aversive learning and memory through learned associations between aversive stimulus (a mild electric shock) and a specific cue (e.g., a tone; cued conditioning) or a context in which electric shock had occurred (contextual conditioning). Once the association is established, the conditioned stimulus (CS, i.e. tone or context) can induce fear response in a similar manner to unconditioned stimulus (US, i.e. electric shock). However, if CS repeatedly presents without combination of US, extinction occurs in normal animals. Fear extinction is usually regarded as a new inhibitory learning after repeated or prolonged CS presentations without the US, which causes a gradual decrease in the magnitude and/or frequency of the conditioned response (i.e. freezing response in FC test). Deficits in such inhibitory learning can be regarded as a hallmark of clinical PTSD.

Studies were performed by PsychoGenics Inc., 100 Philips Parkway, Montvale, N.J. 07645, USA Young adult (about 7 weeks of age), male WKY and Wistar rats purchased from Charles River Laboratory were used in this study. Upon receipt, animals were group-housed (2 per cage) and acclimated for at least 7 days. All rats were examined, handled, and weighed prior to initiation of the study to assure adequate health and suitability. During the course of the study, 12/12 light/dark cycles were maintained. The room temperature was maintained between 20 and 23° C. with a relative humidity maintained around 50%. Rats were randomly assigned to each treatment group. All testing was conducted during the animals' light cycle.

The following compounds were used for this study:

D-cycloserine 30 mg/kg (low dose) and 300 mg/kg (high dose) were dissolved in saline and administered IP 30 min prior to extinction test at a dose volume of 2 ml/kg.

Sertraline 20 mg/kg was dissolved in saline and administered IP 30 min prior to test at a dose volume of 2 ml/kg. When combined with DSC, the combinations were given in a cocktail 30 minute prior to extinction test D-CPP-ene (5 mg/kg) was be dissolved in acidified saline and administered s.c 30 min prior to extinction test at a dose volume of 2 ml/kg Lurasidone (Lur, 0.2 mg/kg was dissolved in saline and administered IP 30 min prior to test at a dose volume of 1 ml/kg Quetiapine (QTP, 10 mg/kg) was dissolved in acidified saline and administered s.c 30 min prior to test at a dose volume of 1 ml/kg The experiment was conducted in the fear conditioning system manufactured by Coulbourn Instruments (PA, USA). Animal's body movements are captured with a video system and the FreezeFrame software, and freezing is analyzed automatically by the FreezeView software (Coulbourn Instruments, PA, USA).

Fear Conditioning Training:

Animals were exposed to 5 CS-US pairings of a 10 sec tone (70 dB conditioned stimulus/CS) co-terminating with a brief electric shock (0.5 mA for 1.0 sec unconditioned stimulus/US). The 5 CS-US pairings are separated by a 60 sec interval with the first CS at 120 s. The rats stage in boxes for one minute after the last shock before being moved out.

Extinction Training:

Extinction training was conducted twice at 24 and 72 hr post FC training. A cued FC extinction paradigm was applied. The extinction training was conducted in the "cylinder", a changed context which is different from the boxes of FC training. The extinction training lasted 32-40 min, including 8-10 identical bins. Each bin includes a 2 min tone period followed by a 2 min no-tone period (inter-trial interval, ITI).

Percent freezing during bins 7-8 of extinction trainings (24 hr and 72 hr) was used to evaluate effectiveness of treatment. Data were analyzed by one-way analyses of variance (ANOVA), with treatment/group and extinction stage (cues or bins) set as factors. Fisher LSD method was used in Post hoc comparisons if applicable.

WKY differed from control (Wistar) rats based on degree of freezing behavior following cue administration across days 1 and 3, with a prominent difference in the number of animals that showed freezing behavior to >85% of stimuli (F=24.6, df=1.76, p<0.0001) (Table 1).

Pharmacological studies were performed with WKY rats only and are shown in Table 2. There was a highly significant treatment effect on freezing behavior across days (F=9.24, df=9,362, p<0.0001). The effect of day was marginally significant (F=3.24, dt=1,362, p=0.07). The day by treatment effect was non-significant (F=0.99, df=9,362, p=0.45). In post-hoc testing, high-dose (300 mg/kg) DCS (LSD p<0.001), sertraline alone (LSD p=0.023) and combined high-dose DCS+Sertraline (LSD p=0.023) all produced significant reduction in freezing behavior relative to vehicle across days. By contrast, low-dose DCS (30 mg/kg) had no significant effect on freezing behavior (p=0.3). The difference in effect between low dose and HD-DCS was significant at trend level (p=0.08).

As opposed to high-dose DCS, the competitive NMDAR antagonist D-CPPene (p=0.009) and the atypical antipsychotics lurasidone (p=0.1) and quetiapine (p=0.009) tended to increase freezing behavior. High-dose DCS tended to decrease freezing when added to lurasidone (p=0.09), but was without statistical effect in combination with quetiapine (p=0.3).

These findings represent the first demonstration that NMDAR antagonists may reduce re-experiencing, avoidance and increased arousal (PTSD-related) behaviors in rodents. Notably, the anti-PTSD effects of D-cycloserine were selectively induced in rodents by administration of a dose of 300 mg/kg (i.e. a dose of D-cycloserine know to produce an NMDAR antagonist effect), and were not observed at a dose of 30 mg/kg (i.e.

a dose of D-cycloserine known to produce NMDAR agonist effects). Moreover, the effect persisted in the presence of the SSRI sertraline, but not in the presence of the 5-HT2A receptor antagonists lurasidone or quetiapine. The competitive NMDAR antagonist D-CPPene produced an increase rather than decrease in freezing behavior, suggesting unexpected beneficial effect of glycine-site vs. glutamate-site antagonism of NMDAR function.

TABLE 1

Percentage animals showing freezing behavior >85% of the time in response to cue stimuli across day 1 and 3 following fear conditioning by strain of rat (Wistar-Kyoto (WKY) vs. Wistar)

| strain# | N observations | Mean | Std. Deviation | Std. Error Mean | |
|---|---|---|---|---|---|
| Wistar (control) | 32 | 0.000 | 0.000 | 0.000 | — |
| Wistar Kyoto (WKY) | 64 | 0.375 | 0.488 | 0.061 | <0.0001 |

TABLE 2

Percentage WKY animals showing freezing behavior >85% of the time in response to cue stimuli across day 1 and 3 following fear conditioning by condition.

| | N observations | Mean | Std. Deviation | Std. Error | Direction of change | P value vs. Vehicle |
|---|---|---|---|---|---|---|
| Vehicle | 64 | 0.375 | 0.488 | 0.061 | — | — |
| DCS300 | 62 | 0.113 | 0.319 | 0.041 | Decrease | 0.001 |
| DCS30 | 32 | 0.281 | 0.457 | 0.081 | — | 0.33 |
| Sertraline | 32 | 0.156 | 0.369 | 0.065 | Decrease | 0.023 |
| DCS + Sertraline | 32 | 0.156 | 0.369 | 0.065 | Decrease | 0.023 |
| DCPPene | 32 | 0.625 | 0.492 | 0.087 | Increase | 0.009 |
| Lurasidone | 32 | 0.531 | 0.507 | 0.090 | Increase | 0.10 |
| Lur + DCS | 32 | 0.344 | 0.483 | 0.085 | Increase | 0.74 |
| QTP | 32 | 0.625 | 0.492 | 0.087 | Increase | 0.009 |
| QTP + DCS | 32 | 0.719 | 0.457 | 0.081 | Increase | <0.001 |

DCS = D-cycloserine

Example 2: Reversal of NMDAR Antagonist Psychotomimetic Effects by Antidepressants The previous example shows the treatment of PTSD symptoms with combined NMDAR antagonists and anti-depression agents. A known concern of NMDAR antagonist treatment, however, is increased liability for psychosis, which may be modeled in rodents using behavioral hyperactivity assays. In this example, unexpected synergistic effects of combined treatment with NMDAR antagonists and anti-depression agents as shown.

For this study, psychomotor effects of D-cycloserine were assessed using the rodent open field test following D-cycloserine administration, in the presence or absence of antidepressant agents.

All testing was performed at PsychoGenics Inc, 765 Old Saw Mill River Road, Tarrytown, N.Y. 10591, USA.

Male C57BL/6J mice (8 weeks old) from Jackson Laboratories (Bar Harbor, Me.) were used. Upon receipt, mice were assigned unique identification numbers (tail marked) and were group housed in OPTImice cages. All animals were acclimated to the colony room for 1 week prior to testing. During the period of acclimation, animals were examined on a regular basis, handled, and weighed to assure adequate health and suitability. Animals were maintained on a 12/12 light/dark cycle. The room temperature was maintained between 20 and 23° C. with a relative humidity maintained between 30% and 70%. Chow and water were provided ad libitum for the duration of the study. All testing was performed during the animal's light cycle phase.

Test compounds included:

D-cycloserine (300 mg/kg) was dissolved in PTS vehicle (5% PEG200: 5% Tween80: 90% NaCl) and administered IP at a dose volume of 10 mL/kg in the open field test.

Bupropion (10 mg/kg) was dissolved in saline and administered IP at a dose volume of 10 mL/kg 30 minutes prior to D-cycloserine in the open field test.

Desipramine (10 mg/kg) was dissolved in saline and administered IP at a dose volume of 10 mL/kg 30 minutes prior to D-cycloserine in the open field test Sertraline (20 mg/kg) was dissolved in sterile water and administered IP at a dose volume of 10 mL/kg 30 minutes prior to D-cycloserine in the open field test Venlafaxine (40 mg/kg) was dissolved in saline and administered IP at a dose volume of 10 mL/kg 30 minutes prior to D-cycloserine in the open field test Duloxetine (40 mg/kg) was dissolved in saline and administered IP at a dose volume of 10 mL/kg 30 minutes prior to D-cycloserine in the open field test Fluoxetine (10 mg/kg) was dissolved in saline and administered IP at a dose volume of 10 mL/kg 30 minutes prior to D-cycloserine in the open field test Imipramine (10 mg/kg) was dissolved in saline and administered IP at a dose volume of 10 mL/kg 30 minutes prior to D-cycloserine in the open field test Citalopram (10 mg/kg) was dissolved in saline and administered IP at a dose volume of 10 mL/kg 30 minutes prior to D-cycloserine in the open field test Levomilnacipran (40 mg/kg) was dissolved in sterile water and administered IP at a dose volume of mL/kg 30 minutes prior to D-cycloserine in the open field test Milnacipran (40 mg/kg) was dissolved in sterile water and administered IP at a dose volume of mL/kg 30 minutes prior to D-cycloserine in the open field test Vilazodone (1 mg/kg) was dissolved in PTS vehicle (5% PEG200: 5% Tween80: 90% NaCl) and administered IP at a dose volume of 10 mL/kg 30 minutes prior to D-cycloserine in the open field test Vortioxetine (10 mg/kg) was dissolved in PTS vehicle (5% PEG200: 5% Tween80: 90% NaCl) and administered IP at a dose volume of 10 mL/kg 30 minutes prior to D-cycloserine in the open field test The open field (OF) test was performed using Plexiglas square chambers (27.3×27.3×20.3 cm; Med Associates Inc., St Albans, Vt.) surrounded by infrared photobeams (16×16×16) to measure horizontal and vertical activities. Mice were brought to the activity experimental room for at least 1 hr acclimation to the experimental room conditions prior to testing. Animals were administered with vehicle, or test compound and placed in the OF. For assessment of D-cycloserine effects, mice were injected with DCS prior to entry into the test chamber, and activity was monitored for 60 min. Alternately, vehicle or D-cycloserine was administered 30-min prior to challenge with amphetamine (4 mg/kg) or phencyclidine (5 mg/kg), and activity was summed for 60 min following vehicle or D-cycloserine administration. For other conditions, animals were treated with vehicle or anti-depressant agents, following which baseline activity was recorded for 30 minutes. Mice then received DCS injections and were placed back into OF chambers for a 60 minute session. At the end of each OF test session the OF chambers were thoroughly cleaned.

Data were analyzed by analysis of variance (ANOVA) followed by post-hoc comparisons using Fishers's LSD test as appropriate. An effect was considered significant if $p<0.05$.

Results: Dose-response was assessed for 30 min after administration of vehicle or D-cycloserine at doses between 30 and 1000 mg/kg. Across all conditions, there was a highly significant effect ($F=19.0$, $df=3.35$, $p<0.001$). Locomotor activity was not significantly affected by D-cycloserine administered at a dose of 30 mg/kg ($p=0.5$), but was significantly increased by both 300 mg/kg ($p<0.001$) and 1000 mg/kg ($p<0.001$) doses of D-cycloserine (Table 3).

TABLE 3

Summary of Locomotor activity data showing number of animals (N), Mean distance travelled over 30 min (Mean), Standard deviation and statistical comparisons for animals treated with Vehicle or D-cycloserine

| Condition | N | Mean | Std. Deviation | p vs. Vehicle |
| --- | --- | --- | --- | --- |
| Vehicle | 10.0 | 4881.4 | 1165.3 | |
| DCS, 30 mg/kg | 10.0 | 4432.1 | 1712.9 | 0.5 |
| DCS, 300 mg/kg | 10.0 | 7588.5 | 1456.2 | <0.001 |

When conditions were separated according to drug type including NDRIs (buproprion), tricyclic anti-depressants (desipramine, imipramine), SSRIs/SNRIs associated with high serotonergic transport (SERT) inhibition activity (sertraline, venlafaxine, duloxetine, fluoxetine, citalopram) vs. newer agents associated with low serotonergic transport inhibition activity relative to other targets such as norepinephrine transporters (levomilnacipran, milnacipran, vilazodone, vortioxetine), unexpected differences among the drug classes were observed (Table 4).

TABLE 4

Summary of locomotor activity data showing number of animals (N), Mean distance travelled over 60 min (Mean), Standard deviation and statistical comparisons for animals treated with Vehicle or D-cycloserine (DCS)

| Condition | N | Mean | Std. Deviation | P v Traditional SSRI/SNRI |
| --- | --- | --- | --- | --- |
| DCS 300 mg/kg | | | | |
| +Traditional SSRIs/SNRIs | 50.0 | 11307.5 | 8447.0 | — |
| +Bupropion | 10.0 | 11526.9 | 6781.4 | 0.9 |
| +TCAs | 20.0 | 2210.9 | 2216.6 | <0.001 |
| +Low SERT SNRI/atypical | 40.0 | 5698.6 | 4633.8 | <0.001 |

This is the first study of which we are aware to show that D-cycloserine on its own produces locomotor hyperactivity in rodents, consistent with its clinical psychotomimetic effect. Taken together with a prior study showing no significant effect of D-cycloserine administered at a dose of 160 mg/kg (Carlsson et al., J Neural Transm 95:223-233, 1994), these findings demonstrate that psychotomimetic effects are observed preferentially at plasma levels exceeding 25 micrograms/mL (see Example 3).

This is also the first study of which we are aware to show that antidepressants show differential effects on locomotor hyperactivity in the presence of D-cycloserine, with preferential effect noted for agents such as TCAs or the newer antidepressants vilazodone, vortioxetine, milnacipran and levomilnacipran, relative to traditional SSRI/SNRIs or bupropion, a dopamine-norephrine reuptake inhibitor.

Newer SNRIs and atypical antidepressants differ from traditional medications in that they have higher specificity for targets other than the serotonin transporter, and thus are relatively more similar to TCAs. These findings show unexpectedly that newer SNRIs/atypical antipsychotics have preferential beneficial activities in combination with a D-cycloserine-dose associated with plasma levels >25 microgram/mL, and thus show unexpected utility of combinations involving high dose D-cycloserine and newer anti-depressant agents.

Example 3: Synergistic Effects of DCS and Mirtazapine on Marble Burying Behavior in Rodents Marble burying is used as a model for both anxiety disorders, including PTSD, and obsessive-compulsive disorder (OCD), and is most tied to the constructs of active avoidance and anxious arousal.

On individual placement in a cage containing glass marbles, mice have been shown to bury the marbles. Anxiolytic agents such as benzodiazepines decrease the marble burying behaviors in rodents. Here, we hypothesized that NMDAR antagonists and anti-depressants would have synergistic effects on marble burying.

Mice were brought to the activity experimental room for at least one hr acclimation to experimental room conditions prior to testing. Mice were placed individually in clean mouse cages containing approximately 6 cm of hard wood bedding and twenty black marbles placed in spaced rows of 5 for 30 min. Distance traveled during the test was captured by cameras and quantified using Video Tracker Software (ViewPoint Life Sciences Software, France). At the end of the test mice were removed from the cages and the number of unburied marbles was counted. A marble was considered buried if it was covered at least two thirds with bedding.

The following compounds were used. All compounds were administered at a dose volume of 10 ml/kg:

D-cycloserine (Sigma, DSC; 30 and 300 mg/kg) was dissolved in 5% PEG 200: 5% Tween 80: 90% saline (PTS) and administered IP 30 min prior to test at a dose volume of 10 ml/kg.

Mirtazapine (Sigma, 5.5 mg/kg) was dissolved in 5% PEG 200: 5% Tween 80: 90% saline (PTS) and administered IP 30 min prior to test at a dose volume of 10 ml/kg Paroxetine (Sigma, 5 mg/kg) was used as the positive reference in the marble burying test. This compound was dissolved in 20% cyclodextrin and administered IP 30 min prior to test at a dose volume of 10 ml/kg.

Combination DSC (300 mg/kg)+Mirtazapine (5.5 mg) was administered IP as a cocktail in a single injection 30 minutes prior to test at a dose volume of 10 ml/kg.

10 mice were tested in each of the following test groups:
Vehicle (5% PEG200; 5% Tween80; 90% Saline)
Paroxetine (5 mg/kg)
Mirtazapine (5.5 mg/kg)

D-cycloserine (30 mg/kg)
D-cycloserine (300 mg/kg)
D-cycloserine (300 mg/kg)+(Mirtazapine 5.5 mg/kg)

Results of the study are shown in FIG. 1. One-Way ANOVA found a significant treatment effect. Post-hoc comparisons demonstrated that Paroxetine (5 mg/kg) as well as Mirtazapine (5.5 mg/kg) significantly reduced the number of marbles buried compared to vehicle. Treatment of animals with either dose of D-Cycloserine (30 mg/kg, and 300 mg/kg) did not affect this measure. The combination of D-cycloserine (300 mg/kg) and Mirtazapine (5.5 mg/kg) significantly reduced the number of marbles buried compared to vehicle and Mirtazapine (5.5 mg/kg) alone.

These findings demonstrate significant unexpected synergy between DCS, administered at an NMDAR antagonist, 300 mg/kg dose, and the anti-depressant mirtazapine on behaviors related to anxiety, OCD and PTSD, and support combined NMDAR antagonist and anti-depressant treatment of PTSD.

Figure 2:
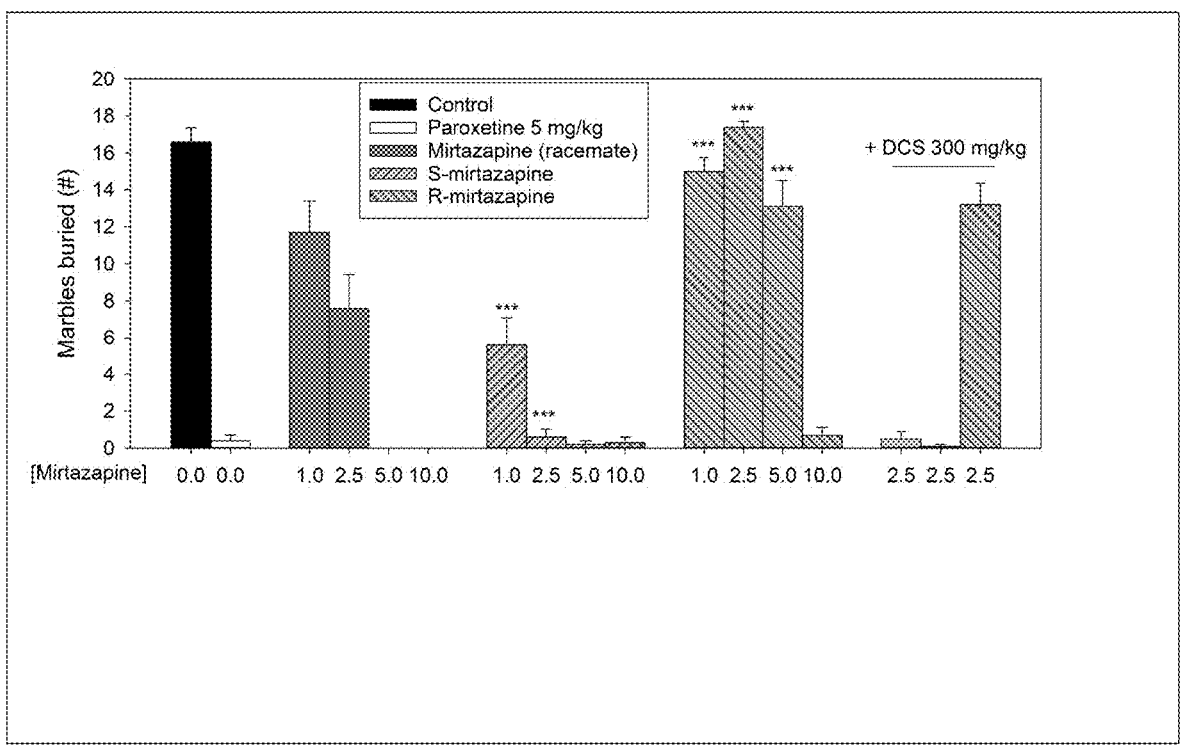
FIG. 2 shows the relative effects of R- and S-isomers of mirtazapine on marble burying, showing greater effects of R- vs S-isomer. ***p<0.001 vs. racemic mirtazapine. 10 mice were treated with either Vehicle (control), Paroxetine (5 mg/kg), S-Mirtazapine (1, 2.5, 5.0, and 10 mg/kg), R-Mirtazapine (1, 2.5, 5.0, and 10 mg/kg), R-Mirtazapine (2.5 mg/kg)+D-cycloserine (300 mg/kg) which was administered by IP 30 minutes prior to test. Distance traveled during the test was captured by cameras and quantified using Video Tracker Software (ViewPoint Life Sciences Software, France). At the end of the test mice were removed from the cages and the number of unburied marbles was counted. A marble was considered buried if it was covered at least two thirds with bedding. An effect was considered significant if p<0.05.

Example 4: Differential Effects of R- and S-Isomers of Mirtazapine on Marble Burying Mirtazapine is a racemic mix of separate R(−) and S(+) isomers. A follow-up study evaluated the relative effects of the two isomers independently. Methods are the same as for Example 3. Test compounds are as follows:
- 5% PEG 200: 5% Tween 80: 90% saline (PTS) was administered IP 30 min prior to test at a dose volume of 10 ml/kg
- Paroxetine (5 mg/kg) was dissolved in saline and was administered IP 30 min prior to test at a dose volume of 10 ml/kg
- D-cycloserine (Sigma, DSC; 300 mg/kg) was dissolved in 5% PEG 200: 5% Tween 80: 90% saline (PTS) and administered IP 30 min prior to test at a dose volume of 10 ml/kg.
- Mirtazapine (Sigma, 1, 2.5, 5.0, and 10 mg/kg) was dissolved in 5% PEG 200: 5% Tween 80: 90% saline (PTS) and administered IP 30 min prior to test at a dose volume of 10 ml/kg
- S-Mirtazapine (TRC, 1, 2.5, 5.0, and 10 mg/kg) was dissolved in 5% PEG 200: 5% Tween 80: 90% saline (PTS) and administered IP 30 min prior to test at a dose volume of 10 ml/kg
- R-Mirtazapine (TRC, 1, 2.5, 5.0, and 10 mg/kg) was dissolved in 5% PEG 200: 5% Tween 80: 90% saline (PTS) and administered IP 30 min prior to test at a dose volume of 10 ml/kg The effects of paroxetine, mirtazapine, S-mirtazapine, R-mirtazapine and D-cycloserine on marble-burying behavior are presented in FIG. 2. One-Way ANOVA found a significant treatment effect. Post-hoc comparisons demonstrated that paroxetine (5 mg/kg), mirtazapine (1, 2.5, 5, and 10 mg/kg), S-mirtazapine (1, 2.5, 5, 10 mg/kg), as well as R-mirtazapine (10 mg/kg) significantly reduced the number of marbles buried compared to vehicle. R-mirtazapine (1, 2.5, and 5 mg/kg), did not affect this measure. Effects of S-mirtazapine were significantly more robust than racemic mirtazapine, whereas effects of R-mirtazapine were less robust (FIG. 2), showing superiority of S-isomer over the racemate for treatment of anxiety-related conditions including OCD and PTSD.

Across the 3 mirtazapine formulations (racemate, R-, S-) there was a highly significant main effect of DCS treatment ($F=27.2$, $df=1.54$, $p<0.001$) supporting prior findings. Mirtazapine (2.5 mg/kg)+DSC (300 mg/kg) combination significantly reduced number of marbles buried compared to mirtazapine (2.5 mg/kg) alone ($p<0.01$). Additionally, the combination of R-mirtazapine (2.5 mg/kg)+DSC (300 mg/kg) significantly reduced number of marbles buried compared to combination of R-mirtazapine (2.5 mg/kg)+ PTS vehicle ($p<0.01$). In the presence of S-mirtazapine, floor level effects were observed in both the absence and presence of DCS, so no comparisons could be performed.

Example 5: Pharmacokinetics of DCS in Rodent

In order to assess the relationship between behavioral effects and plasma DCS levels in rodents, a pharmacokinetic study of DCS was conducted. Male C57BL/6J mice (8 weeks old) from Jackson Laboratories (Bar Harbor, Me.) were used. Upon receipt, mice were assigned unique identification numbers (tail marked) and were group housed in OPTImice cages. All animals were acclimated to the colony room for 1 week prior to testing. During the period of acclimation, animals were examined on a regular basis, handled, and weighed to assure adequate health and suitability. Animals were maintained on a 12/12 light/dark cycle. The room temperature was maintained between 20 and 23° C. with a relative humidity maintained between 30% and 70%. Chow and water were provided ad libitum for the duration of the study. All testing was performed during the animal's light cycle phase.

For these studies, DCS (30, 100, 300, 500 and 1000 mg/kg) was dissolved in PTS vehicle (5% PEG200: 5% Tween80: 90% NaCl) and administered IP at a dose volume of 10 mL/kg.

8 mice were used in each of the following treatment groups, per time point:
- D-cycloserine 30 mg/kg
- D-cycloserine 100 mg/kg
- D-cycloserine 300 mg/kg
- D-cycloserine 500 mg/kg
- D-cycloserine 1000 mg/kg Sample were collected at 30, 60 and 120 min from separate animals. Mean plasma levels across the 30-120 min timepoint was used for analysis. At each time point, trunk blood was collected in tubes containing K2EDTA and kept on ice for short-term storage. Within 15 minutes of blood collection, tubes were centrifuged for 10 minutes at 10,000 RPM in a refrigerated centrifuge. The supernatant (plasma) was extracted and transferred to pre-labeled tubes on dry ice. Samples were stored at approximately −80° C. until analyses.

Analysis of DCS in plasma and brain samples were performed utilizing an UPLC/MS/MS system consisted of an Acquity UPLC chromatographic system and a Quattro Premier XE triple quad mass spectrometer, both from Waters. Isolation of DCS was achieved using a 5 minute (total run time) HILIC methodology which provided an LLOQ of 5 ng/mL.

DCS standards for plasma sample analysis were prepared in mouse plasma which were subsequently filtered (3 kDa cutoff Amicon filter) and then diluted prior to analysis by combining 5 μL of filtrate with 45 μL of a 1.0 ng/mL D9-Ach internal standard solution prepared in 10% water/acetonitrile. The range of standards utilized was 1.0-1000 ng/mL. Plasma samples were prepared in the same manner but with 10 μL of sample and 90 μL of the internal standard mix to provide 100 μL of sample after dilution for triplicate analysis.

Detection of the analyte was performed by monitoring unique fragments formed from the parent ion of DCS (parent 102.7 Da to two fragments 74.7, 57.7 Da). The internal standards D9-Ach (parent 154.95DA to fragment 86.7DA) was incorporated into the samples to correct for sample matrix and instrument variability providing a more robust data set.

Figure 3:
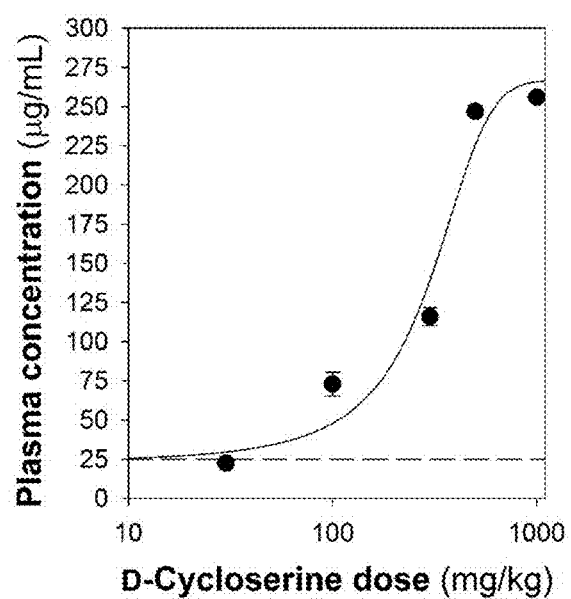
FIG. 3 shows the pharmacokinetics of DCS in rodent. 8 mice were treated with DCS at 30, 100, 300, 500 and 1000 mg/kg which was administered by IP in order to determine what dose produces and effect of DCS plasma levels of >25 micrograms/mL Shown on the graph is plasma (±sem) DCS level vs. dose.

Results of the experiment are shown in FIG. 3. As indicated, the 30 mg/kg dose of DCS produced a plasma level numerically below 25 microgram/mL, although the difference was not statistically significant (p=0.2). At 100 mg/kg and above concentrations were significantly >25 microgram/mL (p<0.01). These findings demonstrate that effects produced by 300 mg/kg DCS in prior examples reflect consequences of DCS plasma levels of >25 micrograms/mL.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method for treatment of post-traumatic stress disorder, (PTSD), or the symptoms thereof, comprising:
    parenterally administering ketamine to a subject in need thereof, followed by administering to the subject a pharmaceutical formulation comprising:
    D-cycloserine administered at a dosage of ≥500 mg/d to ≤1000 mg/d, and formulated to produce blood levels in excess of 25 microgram (μg)/mL, and
    an anti-depression or anti-psychosis agent,
    thereby treating the PTSD, or symptoms thereof.

2. The method of claim 1, wherein the anti-depression agent is selected from the group consisting of a tetracyclic antidepressant (TeCA), selective serotonin reuptake inhibitor (SSRI), a serotonin/norepinephrine reuptake inhibitor (SNRI), a Noradrenaline and specific serotonin agent (NaSSa), an atypical antidepressant, a 5-HT2A antagonist and combinations thereof.

3. The method of claim 1, wherein the anti-depression or anti-psychosis agent is selected from the group consisting of sertraline, paroxetine, and quetiapine.

4. The method of claim 1, wherein the anti-depression agent is selected from the group consisting of imipramine, amitryptyline, amoxapine, bupropion, citalopram, clomipramine, desipramine, desvenlafaxine, duloxetine, escitalopram, fluoxetine, fluvoxamine, levomilnacipran, maprotiline, mianserin, milnacipran, mirtazapine, nefazodone, paroxetine, sertraline, setiptiline, trazodone, venlafaxine, venlafaxine XR, dapoxetine, indalpine, vilazodone and vortioxetine.

5. The method of claim 1 wherein the anti-depression agent is selected from the group consisting of S-(+)-mirtazapine, R-(−)-mirtazapine, and a racemic mixture thereof.

6. The method of claim 1, wherein the anti-depression or anti-psychosis agent is a selective 5-HT2A receptor antagonist or inverse agonist.

7. The method of claim 1, wherein the anti-depression or anti-psychosis agent is selected from the group consisting of volinanserin, pruvanserin, eplivanserin, and pimavanserin.

8. The method of claim 1, wherein the anti-depression or anti-psychosis agent is selected from the group consisting of aglomelatine, Eplivanserine, Lonasen, Edivoxetine, lisdexamfetamine, sacomeline, and clouracetam.

9. The method of claim 1, wherein the ketamine is administered intravenously, intranasally or subcutaneously.

10. The method of claim 1, wherein the ketamine is the specific enantiomer S-ketamine or R-ketamine.

* * * * *